United States Patent [19]

Arnold et al.

[11] Patent Number: 6,017,526

[45] Date of Patent: *Jan. 25, 2000

[54] GERMANIUM YEAST HUMAN DIET NUTRITIONAL SUPPLEMENT

[75] Inventors: Michael Arnold, Irvine; Ping Yang, Fullerton, both of Calif.

[73] Assignee: Viva America Marketing, Inc., Costa Mesa, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/661,089

[22] Filed: Jun. 10, 1996

Related U.S. Application Data

[60] Provisional application No. 60/006,339, Nov. 8, 1995.

[51] Int. Cl.[7] ............................. C12N 1/18; C12N 1/16
[52] U.S. Cl. ..................... 424/93.51; 424/617; 424/600
[58] Field of Search ............................. 424/93.51, 617, 424/600; 514/492

[56] References Cited

U.S. PATENT DOCUMENTS 3,793,455  2/1974  Asai et al. ................. 514/492
5,386,046  1/1995  Arnold ....................... 556/89

FOREIGN PATENT DOCUMENTS 3345211     6/1985   Germany.
53-127882  11/1978   Japan.
53-130483  11/1978   Japan.

OTHER PUBLICATIONS

Barnett J.A. et al. Yeasts Characteristics and Identification, Cambridge University Press. 2d Ed. 1990, pp. 595–597.

*Primary Examiner*—Jean C. Witz
*Attorney, Agent, or Firm*—Lyon & Lyon LLP

[57] ABSTRACT

Germanium-containing compounds are known to have certain therapeutic and prophylactic properties when introduced to the human body, including chemotherapeutic qualities and stimulation of the immune system. The present invention discloses human dietary supplements containing a metabolizable form of germanium-containing yeast, and methods of preparation and use thereof. Although some germanium compounds are known to be toxic, the germanium-yeast product used in the nutritional supplements of the invention are in a form which is more pure, less toxic, and metabolized more readily by the human body.

22 Claims, No Drawings

GERMANIUM YEAST HUMAN DIET NUTRITIONAL SUPPLEMENT

CROSS-REFERENCE TO RELATED APPLICATION

The is a continuation-in-part of co-pending provisional application Ser. No. 60/006,339 filed Nov. 8, 1995.

FIELD OF INVENTION

This invention relates to the field of human dietary supplements, and more specifically to improved human dietary supplements comprising yeast containing substantial amounts of intracellular germanium.

BACKGROUND

Germanium-containing compounds are known to have therapeutic and prophylactic properties when introduced to the human body. For example, use of a specific compound of germanium, carboxyethylgermanium sesquioxide ($Ge_{cD6}H_{12}O_7$), to supplement the human diet has been shown to have chemotherapeutic value. [Asai, K., *Miracle Cure: Organic Germanium*, Japan Publications, Inc., Tokyo (1980) ("hereinafter Asai")]. It is also known that carboxyethylgermanium sesquioxide can provide the human body with resistance to the common cold. [See, Nakao Ishida, et. al., U.S. Pat. No. 4,595,882]. Carboxyethylgermanium sesquioxide is also used as a dietary supplement for treatment of hypertension. [See, Asai, U.S. Pat. No. 3,793,455]. Stimulating the human immune system, and more particularly stimulating the production of interferon, are also believed to be important roles of carboxyethylgermanium sesquioxide. [See, Asai].

A drawback to using some forms of germanium as a food supplement or chemotherapeutic agent is the inherent toxicity attributed to inorganic germanium compounds, such as germanium dioxide ($GeO_2$) and metallic germanium. In contrast to such forms of germanium, carboxyethylgermanium sesquioxide is non-toxic to the human body, having LD50 values in excess of 5 g/kg.

There are two major drawbacks of known techniques for the dietary use of carboxyethylgermanium sesquioxide. First, it is difficult to obtain the compound in pure form. Since carboxyethylgermanium sesquioxide is a completely synthetic compound, and since most syntheses start with a form of germanium that is toxic to the human body, the ultimate purity of the synthesized product, carboxyethylgermanium sesquioxide, can be in question—especially when produced on a large scale. Second, carboxyethylgermanium sesquioxide produced by known techniques requires high dosage levels. Effective dosage levels for dietary supplementation of carboxyethylgermanium sesquioxide generally range from 15 mg/day to over 1 g/day. [See, Asai, at 55–65]. These high doses of the compound are considered to be necessary since the amount of carboxyethylgermanium sesquioxide that is actually metabolized and used constructively by the human body is unknown. It is conventionally believed that a rather large dosage level is important for maximum benefit, suggesting that an appreciable amount of the ingested germanium is unused by the human body. [See, Asai, at 38–39].

Forms of germanium derived from yeast are believed to be of greater value as dietary supplements or chemotherapeutic agents since these forms of germanium are more readily utilized by the body. Since yeast-derived forms of germanium are possibly more capable of being metabolized than other forms of germanium, less yeast-derived germanium needs to be ingested in order to realize the germanium's desired health benefits.

Yeast preparations containing metal ions are not new. A method of producing yeast-derived sources of metabolizable chromium has been reported. [See, e.g., Skogerson, U.S. Pat. No. 4,348,483]. Beneficial aspects of chromium yeast, and their superior nutritional properties in comparison to inorganic forms of chromium have been established. [See, e.g., Shepard, *Biol. Trace Elem. Res.*, 32:109–113 (1992), reporting the use of chromium yeast for potentiation of insulin action in adipocytes from rats]. Selenium metal, usually highly toxic when administered in inorganic form such as $SeO_3Na_2$, has been shown to be more effective nutritionally when ingested as a yeast-derived substance. [See, e.g., Baerwald, *Gordian*, 94(11):169–173 (1994)].

A method for preparing germanium-derived yeast has been taught by Komatsu, JP 77-46138770420. However, this method involves the preparation of germanium yeast using a highly toxic form of germanium, $GeO_2$, as the source of germanium for the feed and cultivation of the yeast. The major shortcoming of the method of Komatsu is that the yeast produced by the method has an appreciable content of highly toxic non-metabolizable germanium, and is therefore not useful as a human dietary supplement.

There remains a need in the art for an improved method for the preparation of germanium yeast where: (1) the yeast product is essentially non-toxic to the human body; and (2) the chemical form of germanium produced by the germanium yeast is highly metabolizable by the human body, and thus a useful and significantly improved agent for the nutritional supplementation of the human diet, and for chemotherapeutic uses.

SUMMARY OF THE INVENTION

The present invention overcomes the shortcomings of the prior art and provides methods for the preparation of yeast containing substantial amounts of intracellular germanium. This metabolizable and essentially non-toxic form of germanium is useful as a dietary supplement and has certain therapeutic and prophylactic properties as described above.

Thus, in a first aspect, the present invention provides a method of preparing yeast that is enriched in germanium content.

In another aspect, the present invention provides a method of preparing a highly active form of germanium that is metabolizable by the human body.

In still another aspect, the present invention provides a method of cultivating Brewer's yeast having enriched germanium, and a method of producing an enriched germanium product derived from the yeast which is essentially non-toxic to the human body.

In yet another aspect, the present invention provides a method for producing Brewer's yeast having an enriched content of germanium and essentially devoid of germanium dioxide or germanium metal.

Still a further aspect of the present invention provides naturally occurring Brewer's yeast compositions which have been processed in such a manner by reaction with carboxyethylgermanium sesquioxide and nutritive growth media as to concentrate the germanium in the yeast. The present invention also provides a dried yeast product having a high germanium activity level and that is essentially non-toxic to the human body and has greater degree of assimilation by the human body.

DETAILED DESCRIPTION OF THE INVENTION

The foregoing objects are achieved by the germanium-yeast product of the present invention that has a high intracellular, organically bound, assimilable germanium content, and which is produced by a process described herein. The germanium yeast product of the present invention produced by this process overcomes the above-described problems in the prior art which may occur from the rather high dose levels of synthetic carboxyethylgermanium sesquioxide by providing a novel form of non-synthetic germanium that is highly metabolizable by the human body, and is, hence, more efficacious as dietary supplement. The dietary supplements of the present invention which contain the germanium-derived yeast are understood to have the nutritional benefits of germanium when administered in humans.

The process for preparing the germanium yeast product of the invention generally comprises contacting live yeast cells in an aqueous suspension under controlled acidic conditions (pH above 4) with aqueous solution containing non-inhibitory amounts of carboxyethylgermanium sesquioxide and suitable growth media to ensure the healthy cultivation of the yeast. The yeast are then incubated, isolated, pasteurized, and dried, yielding a dried yeast product containing intracellular germanium. Another method for production of the desired germanium yeast includes the additional step of incubating the yeast for a short period with the aqueous solution of carboxyethylgermanium sesquioxide before growth phase is induced.

More particularly, the present invention in broad form includes a process for producing a germanium yeast which comprises:

1. contacting live yeast cells to an aqueous solution of carboxyethylgermanium sesquioxide;
2. incubating this suspension for about 5 minutes to about 30 minutes;
3. inducing growth by adding growth media and incubating the yeast for sufficient time to allow for growth;
4. isolating and concentrating the yeast cells from the aqueous growth medium;
5. washing the recovered yeast cells to rid the suspension of extracellular germanium; and
6. pasteurizing and drying the washed yeast cells containing a substantial amount of intracellular germanium ion.

Another preparatory method of the present invention is similar to above but where step (2) is eliminated.

The yeasts employed in the process of the present invention are preferably food grade or edible yeasts, and most preferably Saccharomyces cerevisiae (Baker's yeast). Such yeasts may be commercially available such as, for example, Baker's yeast [Red Star]. Other yeasts which may be used include Torula Utilis and Brewer's yeast *Saccharomyces carlsbergensis* or by its preferred name, *S. uvarum* [Red Star].

The germanium used to treat the yeast is carboxyethylgermanium sesquioxide in concentrations of about 100 ppm to about 30,000 ppm, more preferably from about 500 ppm to about 25,000 ppm, and most preferably from about 1,000 ppm to about 20,000 ppm. A method for the production of pure carboxyethylgermanium sesquioxide has been taught by Arnold, U.S. Pat. No. 5,386,046 (hereinafter "Arnold"), and is incorporated herein by reference. Preferably, the carboxyethylgermanium sesquioxide used here is from a pure source, such as that described by Arnold.

This germanium is used to make an aqueous solution of carboxyethylgermanium sesquioxide. The concentration of germanium in the aqueous solution of carboxyethylgermanium sesquioxide may range from about 100 ppm to about 20,000 ppm at a pH between 4 and 7. The carboxyethylgermanium sesquioxide used in the aqueous solution may be diluted in growth medium or in purified water. The yeast is then added to the aqueous solution to absorb the germanium.

The solution containing the yeast and the carboxyethylgermanium sesquioxide is then incubated. This incubation step may last from about 5 to about 60 minutes to allow for the yeast to absorb the germanium, and more preferably from about 5 to about 30 minutes. Incubating the yeast in the presence of the aqueous solution for between about 5 minutes and 30 minutes induces about a 4 to 7 fold increase in the yeast upon incubation in growth medium.

To the aqueous solution, the growth medium is then added and the yeast incubated for from about 4 to about 50 hours to provide for sufficient growth. The nutrients of the growth medium may include, but are not restricted to, a source of carbohydrate such as molasses. Other nutrient salts in the growth medium are exemplified by potassium chloride, magnesium sulfate, and nitrogen, as well as phosphorous sources such as ammonium dihydrogen phosphate, ammonia, and phosphoric acid.

The pH of the growth medium is essentially in the mild acid range, particularly from about 4 to about 7, or more preferably about 4.5 to about 6, and most preferably from about 5 to about 6. The pH may be adjusted by the addition of a base, such as NaOH, or by the addition of an acid, such as sulfuric acid. For example, when germanium sesquioxide is dissolved in water, 20% NaOH may be used to adjust the pH. As another example, when molasses is used in the growth medium, sulfuric acid may be used to adjust the pH. For some media, as with malt extract, for example, no adjustment of the pH may be necessary. The ability to adjust the pH to the specified ranges is within the skill of the art. The temperature of the growth medium should be between 20° C. and 40° C., more preferably from about 25° C. to about 35° C., and most preferably from about 28° C. to about 32° C.

The time required for the growth phase of the yeast should allow for the intracellular germanium content of the yeast to reach a significant level. By significant level, it is meant that the yeast cells multiply from at least about a 1 fold increase (100% increase) to about 7 fold increase, and preferably to about a 4 fold increase. The yeast growth or fermentation is usually carried out over a period of time from at least about 4 to about 50 hours to achieve the desired growth.

After the yeast cells have multiplied in the growth phase to produce yeast cells with the desired concentration of intracellular germanium, the yeast is recovered, concentrated by centrifugation or other equivalent means, and washed successively with water to remove extracellular carboxyethylgermanium sesquioxide, as well as other solubles. The resulting yeast cream of washed yeast cells has a significant amount of intracellular germanium content and is then pasteurized and dried to kill the yeast. Processes for drying the yeast include drum drying and other techniques known in the art. The preferred concentration of intracellular germanium in the dried yeast is from about 800 $\mu$g to about 4,000 $\mu$g germanium per gram of dried yeast solids. The resulting yeast powder is then ready for use as a dietary supplement of organically bound, assimilable germanium.

To prepare the yeast compositions of the invention for use as either a dietary supplement or a therapeutic agent, the dried yeast product is combined as the active ingredient in intimate admixture with a suitable carrier according to conventional compounding techniques. This carrier may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, and tablets). Controlled release forms may also be used. Because of their ease in administration, tablets, pills, and capsules represent the most advantageous oral dosage unit form, in which case solid pharmaceutical carriers are employed. If desired, tablets may be sugar coated or enteric coated by standard techniques.

For parenteral products the carrier will usually comprise sterile water, although other ingredients may be included, for example, to aid solubility or for preservation purposes. Injectable suspensions may also be prepared, in which case appropriate liquid carriers, suspending agents, adjuvants, and the like may be employed.

A composition of the present invention is generally effective when parenterally administered in amounts ranging from about 50 µg germanium/dose (1 dose per body weight of about 75 kg) to about 200 µg germanium/dose of composition. This is equivalent to about 5 mg/dose to about 1 g/dose of the dried yeast germanium-containing product. When orally administered, the compositions of the present invention are generally effective in approximately the same amounts as the compositions of the present invention administered parenterally. Efficacy of the germanium-yeast compositions at these dosages makes the compositions particularly well suited for formulations in tablet size for oral administration. The above dosage ranges are likely to be administered at varying periods for humans, for example, from twice daily administration to administration at least 5 times per week. However, ultimately, the dosage regiment will depend upon the particular needs of the user.

The following examples illustrate the preferred embodiments of the invention. The examples are illustrative only and do not limit the scope of the invention.

EXAMPLE 1

In this example, Baker's yeast [Red Star] (at 1% solids) was cultivated using 1.0 L of molasses growth medium (or alternatively, malt extract broth) containing 20,000 ppm of carboxyethylgermanium sesquioxide [germanium ferron, Westar Nutrition] at pH of 5.2. This was incubated at 29° C. for 48 hours. This mixture was centrifuged at 4,000 rpm for 15 minutes and the yeast mass was washed five times with 200 mL of deionized water, and then isolated by filtration through a 0.22 micron cellulose acetate membrane [Corning bottle top filer]. This yeast mass was dried in an air flow oven at 80° C. for 6 hours to yield 6.8 g of dried yeast mass having a germanium concentration of 780 µg/gram of yeast. The germanium concentration was determined by ICP technique.

The ICP technique involves the dissolution of dried biomass (i.e., dried germanium-yeast product) in a ratio of 200 mg biomass to 1.6 mL $H_2SO_4$/$HCl_4$/$HNO_3$ (3:1:1, v/v/v) digestion acid, and allowing for digestion for approximately 20 minutes. If the dissolution is incomplete, an additional 0.8 mL of digestion acid may be added until a clear solution is obtained. The sample is then run on a Plasma 400 Sequential Inductively Coupled Plasma Emission Spectroscopy machine [Perkin Elmer] against a reference standard containing germanium, and a concentration of germanium in the sample is thereby obtained.

EXAMPLE 2

Dicarboxygermaniumsesquioxide [Westar Nutrition] (2 g) was dissolved in 985 mL of deionized water by heating to 80° C. for 30 minutes while stirring at 200 rpm. Then, 15 g of malt extract broth [DIFCO] of pH 4.7 was added to the deionized water germanium sesquioxide solution. The resulting mixture was autoclaved at 121° C. for 15 minutes. To this was added 10 g of live Brewer's yeast [Red Star], and the resulting mixture was incubated with gentle swirling (200 rpm) for 30 hours. This mixture was centrifuged at 4,000 rpm for 15 minutes and the yeast mass was washed five times with 200 mL of deionized water, and then isolated by filtration through a 0.22 micron cellulose acetate membrane [Corning bottle top filer]. This yeast mass was dried in an air flow oven at 80° C. for 6 hours to yield 4.5 g of dried yeast mass having a germanium concentration of 629 µg/gram of yeast as measured by ICP technique as described in Example 1.

EXAMPLE 3

Dicarboxygermaniumsesquioxide [Westar Nutrition] (1 g) was dissolved in 985 mL of deionized water by heating to 80° C. for 30 minutes while stirring at 200 rpm. To this was added at pH 4.7, 152 g of molasses, 0.34 g of KCl, 0.34 g of $MgSO_4$ . 7 $H_2O$, and 3.36 g of $NH_4H_2PO_4$. The resulting mixture was autoclaved at 121° C. for 15 minutes. To this was added 10 g of live Brewer's yeast [Red Star] and the resulting mixture was incubated with gentle swirling (200 rpm) for 30 hours. This mixture was centrifuged at 4,000 rpm for 15 minutes and the yeast mass was washed five times with 200 mL of deionized water, and then isolated by filtration through a 0.22 micron cellulose acetate membrane [Corning bottle top filer]. This yeast mass was dried in an air flow oven at 80° C. for 6 hours to yield 5.7 g of dried yeast mass having a germanium concentration of 1500 µg/g of yeast as determined by ICP technique as described in Example 1.

EXAMPLE 4

Dicarboxygermaniumsesquioxide [Westar] (1.5 g) was dissolved in 985 mL of deionized water by heating to 80° C. for 30 minutes while stirring at 200 rpm. To this was added at pH 5.1, 24 g of Potato Dextrose Broth [DIFCO], and the resulting mixture was autoclaved at 121° C. for 15 minutes. To this was added 7.5 g of Brewer's yeast [Red Star], and the resulting mixture was incubated with gentle swirling at 200 rpm for 30 hours. This mixture was centrifuged at 4,000 rpm for 15 minutes and the yeast mass was washed five times with 200 mL of deionized water, and then isolated by filtration through a 0.22 micron cellulose acetate membrane [Corning bottle top filer]. This yeast mass was dried in an air flow oven at 80° C. for 6 hours to yield 8.6 g of dried yeast mass having a germanium concentration of 980 µg/gram of yeast as determined by ICP technique as described in Example 1.

EXAMPLE 5

Dicarboxygermaniumsesquioxide [Westar] (1.0 g) was dissolved in 500 mL of deionized water by heating to 80° C. for 30 minutes while stirring at 200 rpm. This first mixture was autoclaved at 121° C. for 15 minutes. A 500 mL solution for growth medium was prepared by addition of 24 g of Potato Dextrose Broth [DIFCO] at approximately pH 5.2 to 500 mL of deionized water, the resulting second mixture was autoclaved at 121° C. for 15 minutes. To the first mixture was added 10 g of Brewer's yeast [Red Star], and the resulting mixture was incubated at 30° C. for 30 minutes, and then 100 mL of the second mixture was added and the resulting mixture was incubated with gentle swirling at 200 rpm for 2 hours. After 2 hours, an additional 150 mL of the second mixture was added, and this mixture was swirled at 29° C. for 2 hours. Finally, the remaining 250 mL of growth medium was added, and the resulting mixture was swirled at 200 rpm for an additional 11 hours. This resulting mixture was centrifuged at 4,000 rpm for 15 minutes and the yeast mass was washed five times with 200 mL of deionized water, and then isolated by filtration through a 0.22 micron cellulose acetate membrane [Corning bottle top filer]. This yeast mass was dried in an air flow at 80° C. for 6 hours to yield 56.3 g of dried yeast mass having a germanium concentration of 1875 $\mu$g/gram of yeast as determined by ICP technique as described in Example 1.

EXAMPLE 6

As another example, the present invention may also include producing a nutritional broth that contains germanium to which yeast is added and grown to produce a germanium-yeast product. To prepare nutritional broth containing germanium, 10.0 g of carboxyethylgermanium sesquioxide [Westar Nutrition] is added to 500 mL of distilled water. The solution is then heated to between 60° C. and 70° C. with agitation to dissolve the germanium. The pH is adjusted to 6.8 using 25% NaOH. Then 22.5 g of malt extract broth [DIFCO] is added to the germanium solution, and distilled water is added to bring the entire volume to 1.0 L. The solution is then autoclaved at 110° C. for 15 minutes. The resultant malt extract broth contains 10,000 ppm soluble germanium. It is preferable to prepare this nutritional broth containing germanium immediately before the yeast is to be added.

In this example, the yeast are grown before being added to the nutritional yeast broth. The solution of grown yeast is referred to in this example as the yeast seed culture. The yeast seed culture is prepared by adding *S. cerevisiae* yeast to malt extract agar [DIFCO] at pH 4.5 and incubating at 30° C. for 1–2 days. One slant of the yeast is then added to 100 mL of malt extract broth (pH 4.5) and incubated at 30° C. for one day.

Absorption of germanium by the yeast is accomplished by adding 100 mL yeast seed culture to the 1.0 L malt extract broth containing germanium described above. The mixture is incubated at room temperature for approximately one hour, and then the yeast are grown for 1–2 days while shaking at 150 rpm and 30° C.

The yeast are then recovered by centrifugation at 3900 rpm for 5 minutes. The recovered yeast cells are then washed once with 50 mL of a 0.01 M $Na_2HPO_4$ and 0.1 M EDTA solution, and then centrifuged at 5000 rpm for 15 minutes. The wash of the yeast cells is repeated three times with 50 mL of distilled water, centrifuging at 5000 rpm for 15 minutes in between each wash.

Lastly, the wet yeast cream which is recovered is conventionally dried at approximately 100° C. for 2 to 3 hours to yield 4.1 g of dried yeast mass having a germanium concentration of 967 $\mu$g/gram of yeast as determined by ICP technique as described in Example 1.

Numerous modifications and variations of the present invention are included in the above-identified specification and are expected to be obvious to one of skill in the art. It is also intended that the present invention cover modifications and variations of the compositions and method for using them to accomplish their claimed uses within the scope of the appended claims and their equivalents.

We claim:

1. A method for producing a germanium-enriched dried yeast product comprising the steps of:

contacting live yeast cells with an aqueous solution containing a germanium compound selected from the group consisting of carboxyethyl germanium sesquioxide and dicarboxygermanium sesquioxide;

incubating said yeast cells in growth medium;

isolating said yeast cells;

washing said isolated yeast cells to remove extracellular germanium; and drying yeast cells containing intracellular germanium.

2. The method of claim 1 wherein said contacting step lasts from about 5 minutes to about 60 minutes.

3. The method according to claim 1 wherein said aqueous solution comprises the germanium compound diluted in purified water.

4. The method of claim 1 wherein the pH of the aqueous solution ranges from between about pH 4 to about pH 7.

5. The method of claim 1 wherein the pH of the aqueous solution containing the germanium compound ranges from between about pH 4.5 to about pH 6.

6. The method of claim 1 wherein the pH of the aqueous solution containing the germanium compound ranges from between about pH 5 to about pH 6.

7. The method of claim 1 wherein the concentration of the germanium compound ranges from between about 100 ppm to about 30,000 ppm.

8. The method of claim 1 wherein the concentration of the germanium compound ranges from between about 500 ppm to about 25,000 ppm.

9. The method of claim 1 wherein the concentration of the germanium compound ranges from between about 1,000 ppm to about 20,000 ppm.

10. The method of claim 1 wherein the germanium compound contained in said aqueous solution is substantially pure.

11. The method of claim 1 wherein said yeast cells are edible.

12. The method of claim 11 wherein said yeast is selected from the group consisting of *Saccharomyces cerevisae, Torula Utilis,* and *Saccharomyces uvarum*.

13. The method of claim 1 wherein said growth medium includes nutrients selected from the group consisting of molasses, malt extract broth, potato dextrose broth, potassium chloride, magnesium sulfate, nitrogen, ammonium dihydrogen phosphate, ammonia, and phosphoric acid.

14. The method of claim 1 wherein said incubating step lasts from about 4 to about 50 hours.

15. The method of claim 1 wherein said incubating step is conducted at a temperature from between about 20° C. and about 40° C.

16. The method of claim 1 wherein said incubating step is conducted at a temperature from between about 25° C. to about 35° C.

17. The method of claim 1 wherein said incubating step is conducted at a temperature from between about 28° C. to about 32° C.

18. A dried yeast product containing germanium produced by the method of claim 1.

19. The dried yeast product of claim 18 having a concentration of intracellular germanium from about 500 μg to about 3,000 μg germanium per gram of dried yeast solids.

20. A dietary supplement comprising the dried yeast product of claim 18 in a suitable carrier.

21. A method of supplementing the human diet comprising administering an effective amount of the dried yeast product of claim 18 in a suitable carrier.

22. The method of claim 21 wherein the effective amount of the dried yeast product is between about 50 μg/dose to about 200 μg/dose.

* * * * *